United States Patent [19]

Benjamin et al.

[11] 4,382,091

[45] May 3, 1983

[54] STABILIZATION OF 1-SUBSTITUTED IMIDAZOLE DERIVATIVES IN TALC

[75] Inventors: Eric J. Benjamin, Sunnyvale; Maryann O. Lee, Fremont; Lih-Yang Lin, San Jose, all of Calif.

[73] Assignee: Syntex (U.S.A.) Inc., Palo Alto, Calif.

[21] Appl. No.: 259,228

[22] Filed: Apr. 30, 1981

[51] Int. Cl.³ .................... A01N 43/50; A61K 31/415
[52] U.S. Cl. ................................................ 424/273 R
[58] Field of Search ................................... 424/273 R

[56] References Cited

U.S. PATENT DOCUMENTS

| | | | |
|---|---|---|---|
| 4,055,652 | 10/1977 | Walker | 424/273 R |
| 4,078,071 | 3/1978 | Walker | 424/273 R |
| 4,277,475 | 7/1981 | Vickery | 424/273 R |

*Primary Examiner*—Delbert R. Phillips
*Assistant Examiner*—F. T. Moezie
*Attorney, Agent, or Firm*—James M. Kanagy

[57] ABSTRACT

Pharmaceutically acceptable acid addition salts of sulfur containing antimicrobial 1-substituted imidazole compounds can be stabilized in talc-based powders by the addition of a basic metal salt of an inorganic or organic acid.

10 Claims, No Drawings

STABILIZATION OF 1-SUBSTITUTED IMIDAZOLE DERIVATIVES IN TALC

BACKGROUND OF THE INVENTION

1. Field of the Invention

This invention relates to the stabilization of talc-based powder compositions containing a pharmaceutically acceptable acid addition salt of an antimicrobial sulfur containing 1-substituted imidazole compound. Stabilization is achieved by adding a stabilizing amount of a basic metal salt of an inorganic or organic acid.

2. Prior Art

1-Substituted imidazoles and their acid addition salts are but one of a large number of compounds known to be effective for treating fungal, bacterial and protozoal infections. These imidazoles are particularly effective as antifungals, but also have antibacterial and antiprotozoal characteristics.

Generally they are administered to plants, seeds, and soils in the form of sprays, powders or the like. They may be administered to animals in a topical form or by oral administration. One of the more frequently utilized methods of administration is to formulate these antimicrobial imidazoles into powders, particularly powders prepared with a talc diluent. Such powders or dust provide a convenient route for treating soils, disinfecting containers, structures, or the like, for treating seeds and plants, and for treating dermal and other conditions in animals.

Talc-based powder formulations of some sulfur containing L-substituted imidazole acid addition salt compounds were found to show active ingredient degradation during storage under accelerated and normal shelf-life conditions. It has been found that this degradation can be retarded or prevented by adding basic salts of inorganic or organic acids to these talc-based powders.

Talc-based powders containing special ingredients to prevent degradation of a second component are known. For example, U.S. Pat. No. 4,185,086 discloses the addition of polyethylene glycol to talc compositions in order to improve the stability of added fragrances. In another instance, U.S. Pat. No. 3,801,709 describes the use of chelating agents, particularly disodium EDTA or tetrasodium EDTA, as a means for stabilizing talc compositions containing added perfumes. Two Japanese authors, Tetsuya Takahashi and Ryuichi Yamamoto, set out the isomerization effects talc and calcium carbonate excipients have on vitamin $D_2$ in a series of articles published in the periodical Yajugaku Zasshi. There are seven articles in the series which begins at page 914 of vol 89(7), (1969) and running on consecutive pages through page 946 of the same volume of that periodical. None of these references disclose the use of basic metal salts of inorganic or organic acids to prevent talc induced degradation generally, or talc induced degradation of sulfur containing 1-substituted imidazole acid addition salts specifically.

SUMMARY

In the broadest sense, this disclosure relates to stable antimicrobial powder compositions characterized by the presence of a basic metal salt of an inorganic or organic acid.

More specifically, this invention relates to a stable powder composition comprising an antimicrobially effective amount of a pharmaceutically acceptable acid addition salt of a sulfur containing 1-substituted imidazole; a stabilizing amount of a basic metal salt of an inorganic acid, carbonic acid or an alkyl or alkenyl mono or dicarboxylic acid of 1-10 carbon atoms; and at least one diluent which is talc.

In another aspect this invention discloses a method for stabilizing antimicrobial powder compositions which method comprises mixing a stabilizing amount of a basic metal salt of an inorganic acid, carbonic acid, or alkyl or alkenyl mono or dicarboxylic acid of 1-10 carbon atoms with an antimicrobially effective amount of a pharmaceutically acceptable acid addition salt of a sulfur containing 1-substituted imidazole compound and at least one diluent which is talc.

DETAILED DESCRIPTION OF THE INVENTION

The active ingredients of the subject powder compositions are pharmaceutically acceptable acid addition salts of certain 1-substituted imidazoles which retain the antimicrobial activity of the base or themselves demonstrate antimicrobial activity. Of particular interest are those compounds which contain a sulfur substitient or sulfur containing substitient such as, for example, thiol, thioether, thioketal, thioester, thione, thienyl or related sulfur moieties wherein the sulfur atom acts as a bridge between carbon atoms or between carbon and hydrogen at some position in the molecule other than directly on the imidazole ring itself and the sulfur may or may not be substituted with oxygen. The various oxidation states of sulfur are intended to be covered by this invention.

The "acid addition salts" are standard pharmaceutically acceptable acid addition salts such as those enumerated in U.S. Pat. No. 4,078,071, particularly the nitrate salts.

Bases to which this invention has applicability are, for example, those 1-substituted imidazole bases which are represented by the formula:

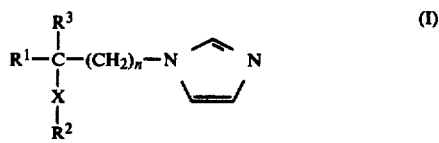

wherein $R^1$ and $R^2$ are independently alkyl (1-12), alkenyl (2-12), substituted or unsubstituted phenyl, substituted or unsubstituted phenyl lower alkyl (1-6), or substituted or unsubstituted phenyl alkenyl (2-6) wherein "substituted" contemplates substitution by one or more alkyl (1-6), halo, lower alkoxy (1-6), trifluoromethyl, nitro or cyano groups; $R^3$ is hydrogen or lower alkyl (1-4); X is sulfur, sulfoxide or sulfone; and n is an integer of from 1 to 4.

Examples of these compounds can be found in U.S. Pat. Nos. 4,036,975; 4,038,409; 4,039,677; 4,045,568; 4,055,652; 4,059,705; 4,150,153; 4,172,141.

Inclusive of representative compounds within the scope of this invention are the 1-substituted imidazole thioethers such as those in U.S. Pat. Nos. 4,036,970; 4,036,973 and 4,036,974.

Additional compounds of the heteroaryl 1-substituted imidazole derivatives such as those disclosed in Belgium Pat. Nos. 841,309 and 849,012. Particularly noteworthy compounds in this group is 1-[2-(2-chloro-3-thienylmethylthio)-2-(2,4-dichlorophenyl)ethyl]imidazole.

All the aforementioned patient citations are incorporated herein by reference.

A preferred group of compounds are those represented by the formula:

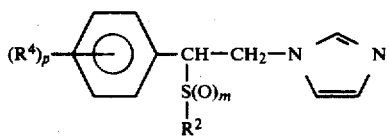
(II)

wherein R² is alkyl, aralkenyl, substituted aralkenyl, alkynyl, cycloalkyl, cycloalkyl alkyl, aralkyl, substituted aralkenyl and substituted aralkyl containing at least one substituent on the aryl moiety selected from the group consisting of halo, lower alkyl, lower alkoxy, trifluoromethyl, nitro and cyano and said substituted aryl containing at least one substituent selected from the group consisting of halo, lower alkyl, lower alkoxy, trifluoromethyl, nitro, amino, acylamino and cyano;

R⁴ is hydrogen, halo, lower alkyl, lower alkoxy, trifluoromethyl, nitro, cyano, thiocyanyl or the group:

in which

R⁵ is alkyl, cycloalkyl, aralkyl substituted aralkyl, aryl, or substituted aryl, said substituted aralkyl and said substituted aryl containing at least one substituent on the aryl moiety selected from the group consisting of halo, lower alkyl, lower alkoxyl, trifluoromethyl, nitro and cyano;

m, n and p are independently selected from the integers zero, 1 and 2; provided that:

the value of m cannot be greater than the value of n except when R⁴ is the group

and R⁵ is aryl or substituted aryl.

One especially preferred group of compounds are those wherein R², R⁴ and p are as previously defined.

Preferred compounds within the above defined subclass are those wherein R⁴ is halo and R² is alkyl, alkenyl, aralkenyl, halo substituted aralkenyl, aralkyl, halo or lower alkoxy substituted aralkyl, aryl or halo or lower alkoxyl substituted aralkyl, aryl or halo or lower alkoxy substituted aryl.

Especially preferred compounds within the group described in the previous paragraph are those wherein R² is alkyl containing 1 to 12 carbon atoms, 2-alkenyl, 3-phenyl-2-alkenyl, halo substituted 3-phenyl-2-alkenyl, benzyl, halo or lower alkoxy substituted benzyl, phenyl or halo lower alkoxy substituted phenyl.

More especially preferred compounds within the group described in the previous paragraph are those wherein (R¹)ₚ is 2,4-dihalo and R is alkyl containing 4 to 10 carbon atoms, halo or methoxy substituted benzyl or halo or methoxy substituted phenyl.

Most especially preferred is a compound within the group described in the previous paragraph which is 1-[2-(4-chlorobenzylthio)-2-(2,4-dichlorophenyl)ethyl]imidazole.

The preferred compounds and those following thereafter are the subject of U.S. Pat. No. 4,055,652 which is incorporated herein by reference.

The term "alkyl" as used in herein refers to a saturated, unbranched or branched acylic hydrocarbon group containing 1 to 20 carbon atoms inclusive, such a methyl, ethyl, n-propyl, isopropyl, n-butyl, i-butyl, n-pentyl, n-heptyl, n-octyl, n-nonyl, n-dodecyl, n-octadecyl and the like. The term "lower alkyl" refers to an alkyl group as previously defined containing 1 to 6 carbon atoms, inclusive. The term "lower alkoxy" refers to groups of the formula lower alkyl—O— wherein the lower alkyl substituent is as previously defined. The term "cycloalkyl" as used herein refers to a saturated monocyclic hydrocarbon group having 5 to 8 ring carbon atoms, such as cyclopentyl, cyclohexyl, cycloheptyl and the like. The term "cycloalkyl alkyl" refers to a cycloalkyl group as previously defined attached to an unbranched acyclic hydrocarbon group containing 1 to 3 carbon atoms, such as cyclopentylpropyl, cyclohexylmethyl, cyclohexylethyl, cycloheptylmethyl and the like. The term "alkenyl" refers to an unbranched or branched acyclic hydrocarbon group having carbon-carbon double bond unsaturation and containing 2 to 12 carbon atoms such as allyl, 2-hexenyl, 3-octenyl, 2-octenyl, 2-decenyl and the like. The term "aralkenyl" refers to a hydrocarbon moiety in which the alkenyl portion containing 2 to 4 carbon atoms is attached to a hydrocarbon group consisting of one or more aromatic rings and containing 6 to 10 ring carbon atoms such as 3-phenyl-2-propenyl and the like. The term "alkynyl" refers to an unbranched or branched acyclic hydrocarbon group having carbon-carbon triple bond unsaturation and containing 2 to 12 carbon atoms, such as 2-propyl, 3-hexynyl, 2-octynyl and the like. The term "aryl" refers to a hydrocarbon group consisting of one or more aromatic rings and containing 6 to 10 ring carbon atoms, such as phenyl and naphthyl. The term "aralkyl" refers to a hydrocarbon moiety in which the alkyl portion contains 1 to 4 carbon atoms and the aryl portion is defined as above. Representative examples of aralkyl groups include benzyl, 3-phenylpropyl and the like. The term "acylamino", i.e. R—C(O)—NH—, refers to substituents containing up to 12 carbon atoms, wherein R in such substituents is methyl, ethyl, i-propyl, n-butyl, pentyl, octyl and the like. The term "halo" as used herein refers to chloro, fluoro and bromo.

Powder compositions prepared according to the teachings of this invention will contain an antimicrobially effective amount of an acid addition salt of one or more of the compounds just described. The amount of active ingredient present in a particular formulation will depend on the level of activity demonstrated by the particular imidazole being confected and the amount of active ingredient to be applied in a particular instance or under particular circumstances.

While the precise amount of active ingredient will be determined at the time of formulation and will be finally dependent on the above enumerated factors, a composition prepared according to the invention as described herein would comprise the active ingredient in an amount between approximately 0.01% and 10% weight/weight (w/w) of the finally prepared powder. A preferred concentration range for the various sulfur containing imidazole acid addition salts described herein would be an amount of about 0.1% to 5% (w/w), but for the compounds represented by formula II it is most preferred to have a concentration of about 1% (w/w).

As set out above, talc induced degradation of sulfur containing 1-substituted imidazole acid addition salt compounds can be controlled and prevented by incorporating basic metal salts of inorganic or certain organic acids into talc-based powders. This idea has application to any of the several classifications of powder types recognized in the formulation arts. While the primary interest of this invention relates to stabilization of topical powders, all talc-containing or talc-based powders such as oral powders, dentifrices, douche powders, insufflations, and triturations having sulfur-containing 1-substituted imidazole acid addition salts can be stabilized by the practice of this invention.

Basic metal salts having utility for the practice of this invention can be chosen from any of the numerous salts of inorganic acids, short chain mono, di or tri carboxylic acids, or salts of the various long-chain fatty acids or sulfonated fatty acids and alcohols and related surfactants known to the formulation arts. Selected salts should be inert in the sense that they themselves would not be expected or intended to act as bacteriacides or bacteriastats or demonstrate any keratolytic action. Additionally, such basic salts would not demonstrate any deleterious or untoward pharmacological effects on the host to which these powders are applied.

A basic metal salt, as that term is used here, should be understood to mean any metal salt of an acid which demonstrates basic properties in either the Bronsted or Lewis sense. It is envisioned that this definition would apply not only to those salts where all protons have been replaced with a mono or polyvalent metal ion but would extend to those metal salts of acids which contain a proton but demonstrate a pH of 7 or greater. Most such salts, especially those of inorganic acids and many organic acids, will be water soluble but water solubility should not be a limiting factor in selecting a basic metal salt for the practice of this invention. Metal salts of surfactants, whether water-soluble or water dispersible are also to be included within the scope of this invention.

Basic metal salts of inorganic acids which are within the scope of this invention are, for example, the various basic alkali metal salts of phosphoric acid such as disodium phosphate, dipotassium phosphate, calcium phosphate, and the like; basic alkali metal salts of orthophosphate, hypophosphate, pyrophosphate, and the like, such as the di and trisodium forms of orthophosphate, the di and tripotassium orthophosphates, magnesium orthophosphate, and magnesium pyrophosphate, sodium or potassium hypophosphate, sodium or potassium pyrophosphate, calcium hypophosphate and calcium orthophosphate including the mono, di and tri calcium forms, calcium pyrophosphate, and mixed alkali metal salts of these various phosphates. The various alkali metal salts of nitric acids such as sodium nitrate, potassium nitrate, calcium nitrate, magnesium nitrate, and the like, can be used in the practice of this invention. Alkali metal salts of sulfuric acid such a sodium sulfate, potassium sulfate, magnesium sulfate, calcium sulfate, and the like have utility herein. Also alkali metal salts of boric acid such as sodium borate or potassium borate may be used.

Additionally there may be used the basic alkali metal salts of various mono, di or tri carboxylic acids. For example, the alkali metal salts of carbonic acid, such as sodium bicarbonate, sodium carbonate, potassium carbonate, potassium bicarbonate, sodium potassium carbonate, magnesium carbonate or calcium carbonate may be used herein. Further, the alkaline metal salts of organic acids, such as formic acid, acetic acid, propionic acid, glycolic acid, lactic acid, pyruvic acid, oxalic acid, malonic acid, succinic acid, malic acid, maleic acid, fumaric acid, tartaric acid, benzoic acid, cinnamic acid, mandelic acid, and the like may be used.

In the practice of this invention it is most convenient to use a basic metal salt of an inorganic acid, carbonic acid or an alkyl or alkenyl mono or dicarboxylic acid of 1-10 carbon atoms. It is preferable to use a basic salt which is an alkali metal salt of sulfuric acid, phosphoric acid, carbonic acid or acetic acid, but it is most preferred to use sodium bicarbonate or potassium acetate to prevent degradation of the active ingredient.

The precise amount of basic salt needed to prevent or control degradation of the active ingredient is some amount which is equal to or slightly greater than the percent weight of active ingredient present in the formulation. For example, when the active ingredient is present in an amount between 0.01% to 10% (w/w) a corollary amount of basic salt would be an amount between 0.05% to 10% (w/w). A preferred amount of basic salt would be that amount which is between 0.5% to 5%, but most preferably, the basic salt will be present in an amount of 1%.

The powder diluent of primary concern in this invention is talc, also known as talcum or french chalk. Lumps of this material are also known as soapstone or steatite. Chemically, it is a finely divided native hydrous magnesium silicate. Talc is a white to grayish-white, very fine odorless, crystalline powder; is unctuous and adheres readily to skin. It is insoluble in water, cold acids or in alkali. Pharmaceutically quality talc is available from numerous manufacturers and fine chemical supply houses.

Powders prepared according to the teachings of this invention will use talc alone or talc in combination with other neutral excipients. Flow enhancing agents such as Cabosil ® or Aerosil ® may be added. Cabosil ® and Aerosil ® are colloidal silica materials marketed by Cabot and Degussa, respectively. Lactose or starch, binding agents, may be added in small amounts if desired. Additionally, materials such as magnesium stearate or stearic acid may be added as lubricants. Perfumes may also be added if desired or where indicated.

The subject antimicrobial powders will contain mostly talc. That is, talc will generally be present in an amount of 50% or greater by weight of the final powder composition. If excipients such as Cabosil ® or Aerosil ® are present, they would be included in an amount of about 0.25-2% by weight, as would lactose or starch. Magnesium stearate or stearic acid may be included in an amount of up to 20% by weight.

The following examples serve to illustrate some of the powder compositions which can be prepared according to the teachings of this invention. These examples are only as exemplary of the various methods and combinations available for practicing this invention and it should be understood that they are not intended to limit in any manner the practice of this invention.

EXAMPLE I

Powders may be prepared by thoroughly mixing the active ingredient and basic metal salt compounds and then confecting the mixture with talc or a talc-based diluent using an appropriate mixing device. For instance, 1 gram of sodium bicarbonate was intimately mixed with 1 gram of 1-[2-(4-chlorobenzylthio)-2-(2,4-dichlorophenyl)ethyl]imidazole nitrate by trituration. This material was then combined with 98 grams of talc and mixed for 30 minutes in a double-cone blender. Using this method the stable powder compositions of this invention may be prepared wherein the basic metal salt is sodium carbonate, sodium acetate potassium acetate or any of the various other salts disclosed herein.

EXAMPLE II

This example illustrates the stabilizing effect sodium bicarbonate demonstrates when added to talc-based powder compositions of antimicrobial active sulfur containing 1-substituted imidazole acid addition salt compounds. A topical powder comprising 1% (w/w) 1-[2-(4-chlorobenzylthio)-2-(2,4-dichlorophenyl)ethyl]imidazole nitrate (sulconazole nitrate), talc and varying amounts of sodium bicarbonate were prepared as noted in Example I. Aliquots were placed in sealed vials and placed in an 80° C. oven until time of assay. These samples were analyzed at the stated time points, giving the results recorded in Table I.

TABLE I
EFFECTS OF SODIUM BICARBONATE ON THE STABILITY OF 1% SULCONAZOLE NITRATE IN TALC

| % NaHCO$_3$ (w/w) | Days at 80° C. | % Labeled Strength* | t$_{90}$ (Days) |
|---|---|---|---|
| 0 | 16 | 45, 36 | 1.7 |
| 0.05 | 39 | 15, 20 | 4.4 |
| 0.10 | 39 | 33, 29 | 4.8 |
| 0.25 | 39 | 40, 91 | 13.7 |
| 0.50 | 39 | 47, 43 | 10.0 |
| 1.0 | 63 | 91 | 51.0 |
| 2.5 | 63 | 92, 91 | 67.0 |

*Initial assay values for batches with 0.25% NaCO$_3$ were 99–100% labled strength.

At 0.05% sodium bicarbonate the t$_{90}$, the time for 10% of the drug to decompose, is approximately 3 times greater than when no sodium bicarbonate is present. The effect becomes more pronounced as the amount of sodium bicarbonate is increased.

EXAMPLE III

The stabilizing effects of a basic metal salt on talc-based powders having sulfur containing 1-substituted imidazoles acid addition salts is illustrated in this example.

Powders comprising 1% (w/w) 1-[2-(4-chlorobenzylthio)-2-(2,4-dichlorophenyl)ethyl]imidazole nitrate (sulconazole nitrate), talc and varying quantities of sodium bicarbonate were prepared as per Example I. Aliquots were placed in sealable vials with 0.1 ml of water. The vials were sealed and placed in an 80° C. oven until time of assay. Results are contained in TABLE II.

TABLE II
SULCONAZOLE NITRATE POWDER STABILIZATION EFFECT OF MOISTURE ON FORMULATIONS CONTAINING NaHCO$_3$

| % NaHCO | % LS SULCONAZOLE NITRATE | |
|---|---|---|
| | 1 wk | 2 wk |
| 0 | 83, 80 | 75, 77 |
| 0.05 | 94, 93 | 91, 91 |
| 1.0 | 98, 97 | 98, 95 |

TABLE II-continued
SULCONAZOLE NITRATE POWDER STABILIZATION EFFECT OF MOISTURE ON FORMULATIONS CONTAINING NaHCO$_3$

| % NaHCO | % LS SULCONAZOLE NITRATE | |
|---|---|---|
| | 1 wk | 2 wk |
| 2.5 | 97, 98 | 95, 97 |

The stabilizing effect of sodium bicarbonate is notable for all time points, particularly where 1% (w/w) or more is present.

What is claimed is:

1. A stable talc-based powder composition comprising 0.01% to 10% (w/w) of an acid addition salt of the compound represented by the formula:

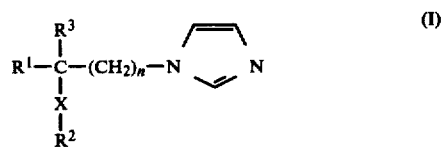

wherein R$^1$ and R$^2$ are independently alkyl (1–12), alkenyl (2–12), substituted or unsubstituted phenyl, substituted or unsubstituted phenyl lower alkyl (1–6), or substituted or unsubstituted phenyl lower alkenyl (2–6), wherein substituted with reference to phenyl refers to phenyl substituted by one or more lower alkyl (1–6), halo, lower alkoxy (1–6), trifluoromethyl, nitro or cyano groups; R$^3$ is hydrogen or lower alkyl (1–6); X is sulfur, sulfoxide or sulfone; and n is an integer of from 1 to 4; 0.05% to 10% (w/w) of a basic metal salt of phosphoric acid, orthophosphoric acid, hypophosphoric acid, pyrophosphoric acid, nitric acid, sulfuric acid, boric acid, carbonic acid, or an alkyl or alkenyl, mono or dicarboxylic acid of 1–10 carbon atoms; and an excipient containing talc in a quantity sufficient to provide a final composition containing at least 50% (w/w) talc.

2. The composition of claim 1 wherein said compound is an PAAA salt of a compound represented by the formula:

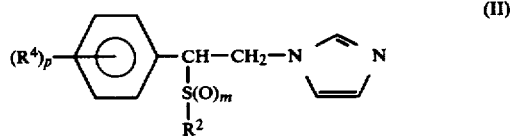

wherein
R$^2$ is alkyl, aralkenyl, substituted aralkenyl, alkynyl, cycloalkyl, cycloalkyl alkyl, aralkyl, substituted aralkenyl and substituted aralkyl containing at least one substituent on the aryl moiety selected from the group consisting of halo, lower alkyl, lower alkoxy, trifluoromethyl, nitro and cyano and said substituted aryl containing at least one substituent selected from the group consisting of halo, lower alkyl, lower alkoxy, trifluoromethyl, nitro, amino, acylamino and cyano;
R$^4$ is hydrogen, halo, lower alkyl, lower alkoxy, trifluoromethyl, nitro, cyano, thiocyanyl or the group:

in which $R^5$ is alkyl, cycloalkyl, aralkyl substituted aralkyl, aryl, or substituted aryl, said substituted aralkyl and said substituted aryl containing at least one substituent on the aryl moiety selected from the group consisting of halo, lower alkyl, lower alkoxyl, trifluoromethyl, nitro and cyano;

m, n and p are independently selected from the integers zero, 1 and 2; provided that:

the value of m cannot be greater than the value of n except when $R^4$ is the group

and $R^5$ is aryl or substituted aryl; and said basic salt is sodium bicarbonate, sodium carbonate, sodium acetate or potassium acetate.

3. The composition of claim 2 wherein sacompound is present in an amount between 0.1% and 5% (w/w); said basic salt is present in an amount between 0.5% and 5% (w/w).

4. The composition of claim 3 wherein said compound is 1-[2-(4-chlorobenzylthio)-2-(2,4-dichlorophenyl)-ethyl]imidazole nitrate; said base is sodium bicarbonate or potassium acetate; and said diluent is talc.

5. The composition of claim 4 wherein said compound is present in an amount of 1% (w/w); said basic salt is present in an amount of 1% (w/w); and said diluent is present in an amount of 98% (w/w).

6. A method for stabilizing a talc-based composition which comprises mixing 0.05% to 10% (w/w) of a basic metal salt of phosphoric acid, orthophosphoric acid, hypophosphoric acid, pyrophosphoric acid, nitric acid, sulfuric acid, boric acid, carbonic acid, or an alkyl or alkenyl mono or dicarboxylic acid of 1-10 carbon atoms with 0.01% to 10% (w/w) of a compound represented by the formula:

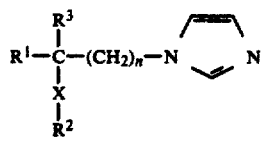

(I)

wherein $R^1$ and $R^2$ are independently alkyl (1–12), alkenyl (2–12), substituted or unsubstituted phenyl, substituted or unsubstituted phenyl lower alkyl (1–6), or substituted or unsubstituted phenyl lower alkenyl (2–6), wherein substituted with reference to phenyl refers to phenyl substituted by one or more lower alkyl (1–6), halo, lower alkoxy (1–6), trifluoromethyl, nitro or cyano groups; $R^3$ is hydrogen or lower alkyl (1–6); X is sulfur, sulfoxide or sulfone; and n is an integer of from 1 to 4; and an excipient containing talc in an amount sufficient to provide a final composition which contains at least 50% (w/w) talc.

7. The method of claim 6 wherein said compound is a PAAA salt of a compound represented by the formula:

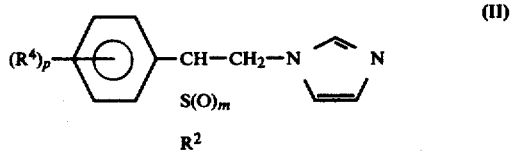

(II)

wherein $R^2$ is alkyl, aralkenyl, substituted aralkenyl, alkynyl, cycloalkyl, cycloalkyl alkyl, aralkyl, substituted aralkenyl and substituted aralkyl containing at least one substituent on the aryl moiety selected from the group consisting of halo, lower alkyl, lower alkoxy, trifluoromethyl, nitro and cyano and said substituted aryl containing at least one substituent selected from the group consisting of halo, lower alkyl, lower alkoxy, trifluoromethyl, nitro, amino, acylamino and cyano;

$R^4$ is hydrogen, halo, lower alkyl, lower alkoxy, trifluoromethyl, nitro, cyano, thiocyanyl or the group:

in which $R^5$ is alkyl, cycloalkyl, aralkyl substituted aralkyl, aryl, or substituted aryl, said substituted aralkyl and said substituted aryl containing at least one substituent on the aryl moiety selected from the group consisting of halo, lower alkyl, lower alkoxyl, trifluoromethyl, nitro and cyano;

m, n and p are independently selected from the integers zero, 1 and 2; provided that:

the value of m cannot be greater than the value of n except when $R^1$ is the group

and $R^5$ is aryl or substituted aryl; and and said basic salt is sodium bicarbonate, sodium carbonate, sodium acetate or potassium acetate.

8. The method of claim 7 wherein said compound is present in an amount between 0.1% and 5% (w/w); said basic salt is present in an amount of 0.5% and 5% (w/w).

9. The method of claim 8 wherein said compound is 1-[2-(4-chlorobenzylthio)-2-(2,4-dichlorophenyl)ethyl-]imidazole nitrate; said basic salt is sodium bicarbonate or potassium acetate; and said diluent is talc.

10. The composition of claim 9 wherein said compound is present in an amount of 1% (w/w); said basic salt is present in an amount of 1% (w/w); and said diluent is present in an amount of 98% (w/w).

* * * * *